United States Patent
Xiao et al.

(10) Patent No.: US 9,144,685 B2
(45) Date of Patent: Sep. 29, 2015

(54) USING FOCAL MYOCARDIAL STIMULATION TO DISTINGUISH SUPRAVENTRICULAR TACHYCARDIA FROM VENTRICULAR TACHYCARDIA

(75) Inventors: Yong-Fu Xiao, Blaine, MN (US); Jeffrey M. Gillberg, Coon Rapids, MN (US); Paul J. DeGroot, Shoreview, MN (US); Eduardo N. Warman, Maple Grove, MN (US); Scott J. Brabec, Elk River, MN (US); John L. Sommer, Coon Rapids, MN (US); Jon F. Urban, Minneapolis, MN (US); Lepeng Zeng, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 279 days.

(21) Appl. No.: 13/357,646

(22) Filed: Jan. 25, 2012

(65) Prior Publication Data

US 2012/0232605 A1    Sep. 13, 2012

Related U.S. Application Data (60) Provisional application No. 61/450,871, filed on Mar. 9, 2011.

(51) Int. Cl.
*A61N 1/00* (2006.01)
*A61N 1/365* (2006.01)
*A61N 1/362* (2006.01)

(52) U.S. Cl.
CPC .............. *A61N 1/365* (2013.01); *A61N 1/3622* (2013.01); *A61N 1/36585* (2013.01)

(58) Field of Classification Search
CPC ......... A61N 1/00; A61N 1/362; A61N 1/365; A61N 1/368
See application file for complete search history.

(56) References Cited

U.S. PATENT DOCUMENTS

| | | |
|---|---|---|
| 5,243,980 A | 9/1993 | Mehra |
| 5,690,681 A | 11/1997 | Geddes |
| 6,035,232 A | 3/2000 | Thong |
| 6,980,860 B2 | 12/2005 | Stadler |
| 7,139,607 B1 | 11/2006 | Shelchuk |
| 7,769,446 B2 | 8/2010 | Moffitt |
| 2006/0058849 A1 | 3/2006 | Chen et al. |
| 2008/0269819 A1 | 10/2008 | Zhou |
| 2009/0259269 A1 | 10/2009 | Brown |
| 2010/0249627 A1 | 9/2010 | Zhang et al. |

FOREIGN PATENT DOCUMENTS

EP     0 597 459 A2     5/1994

OTHER PUBLICATIONS

P0038521.WOU2 (PCT/US2012/022505) PCT Notification of Transmittal of the International Search Report and the Written Opinion of the International Searching Authority. May 10, 2012.

*Primary Examiner* — Christopher D Koharski
*Assistant Examiner* — Elizabeth K So
(74) *Attorney, Agent, or Firm* — Michael C. Soldner (57) ABSTRACT

An apparatus and method to discriminate cardiac events by sensing atrial and ventricular depolarizations having associated refractory periods thereafter. A fast ventricular rate is detected in response to the sensed ventricular depolarizations. Responsive to detecting the fast ventricular rate, at least one stimulus pulse is delivered to atrial tissue within the associated refractory period of the ventricle but outside of an associated refractory period of the stimulated atrial tissue. A ventricular response to the atrial tissue stimulus pulse is determined, and the cardiac event is discriminated based on the ventricular response to the atrial tissue stimulus pulse.

24 Claims, 4 Drawing Sheets

USING FOCAL MYOCARDIAL STIMULATION TO DISTINGUISH SUPRAVENTRICULAR TACHYCARDIA FROM VENTRICULAR TACHYCARDIA

CROSS REFERENCE TO PRIORITY APPLICATION

This application claims priority to U.S. provisional application No. 61/450,871, filed Mar. 9, 2011, and incorporate herein by reference in its entirety.

CROSS-REFERENCE TO RELATED APPLICATION

Cross-reference is hereby made to the commonly-assigned related U.S. application Ser. No. 13/357,659, entitled "USING FOCAL MYOCARDIAL STIMULATION TO DISTINGUISH SUPRAVENTRICULAR TACHYCARDIA FROM VENTRICULAR TACHYCARDIA," to Xiao et al., filed concurrently herewith and incorporated herein by reference in its entirety.

TECHNICAL FIELD

This disclosure relates generally to implantable medical devices and, more specifically, to cardiac electrical stimulation and discrimination of cardiac arrhythmias.

BACKGROUND

Clinical evidence has shown that implantable cardioverter defibrillators (ICDs) reduce mortality, which has led to a significant increase in their use. Patients implanted with an ICD, however, potentially face the problem of defibrillator shocks delivered unnecessarily for rhythms other than ventricular fibrillation or sustained ventricular tachycardia (VT). Unnecessary ICD shocks cause undue pain, psychological disturbance and can potentially induce more serious arrhythmias in some patients. Supraventricular tachycardia (SVT), including atrial fibrillation, atrial tachycardia and sinus tachycardia, are a common cause of unnecessary ICD shocks. The actual cause in a given case can often be ascertained by analysis of data recorded by the ICD. ICD shocks due to SVT being detected as VF or VT can account for some shocks delivered to ICD-implanted patients. Therefore, appropriately distinguishing SVT from VT could lead to a reduction in unnecessary ICD shocks being delivered, without decreasing ICD efficacy.

DETAILED DESCRIPTION

In the following description, references are made to illustrative embodiments. It is understood that other embodiments may be utilized without departing from the scope of the disclosure provided herein. For purposes of clarity, identical reference numbers are used in the drawings to identify similar elements.

In a healthy heart, the sino-atrial (SA) node initiates action potentials which propagate to the whole heart via a conductive system. Compared with the ventricles, the SA node, atria and atrio-ventricular (AV) node are normally excited earlier and recover earlier in the cardiac cycle than the ventricles. In addition, the refractory period of the ventricles continues after the end of the atrial and nodal refractory periods due to longer action potential durations associated with the ventricular myocardium. Therefore, there is a stimulus time window during which the atrial myocardial tissue, SA node and/or AV node, referred to herein collectively as "atrial tissue", may be excited while the ventricles remain refractory to stimulation. The stimulation of the SA node or AV node in the methods described herein is achieved via inducing myocardial cell depolarization in contrast to modulating nodal tissue excitability via stimulating the nerves that innervate the nodal tissue.

Excitation of the atria, SA node and/or AV node during the ventricular refractory period resets the atrial cycle (resets the SA node) and starts a new refractory period in the atrial and AV nodal tissue, without triggering a ventricular contraction. The result is that propagation of a depolarization to the ventricles effective to cause a contraction is delayed until the next subsequent depolarization of the SA node. The inventors have found that delivery of electrical stimulation to atrial tissue during SVT can effectively reset the SA node or block the AV node impulse propagating to the ventricles, resulting in a slowing of up to 50% of the ventricular rate in experimental subjects. In some cases, an SVT can even be terminated by a properly timed atrial stimulus pulse.

The slowing of the ventricular rate during SVT, or termination of SVT, allows the SVT to be reliably discriminated from VT since the atrial tissue stimulation will have no effect on the ventricular rate if the fast ventricular rate is originating in the ventricular chambers. The slowing of the ventricular rate by depolarizing atrial myocardial tissue during ventricular refractory to enable tachycardia discrimination thus has the potential to reduce ICD shocks delivered unnecessarily during SVT.

The delivered atrial stimulus pulses may correspond to typical cardiac pacing pulses or may be pulse bursts having burst envelopes corresponding to the duration and/or morphology of normal cardiac pacing pulses. Longer pulse durations, e.g. 10 ms or more may also be employed. The particular form of the pulse is not critical so long as it triggers a depolarization of the desired atrial tissue. Proper timing of the stimulus pulses within the defined excitation window is important to assure that the desired effect is produced, i.e. atrial myocardial depolarization during ventricular refractory, without induction of arrhythmias.

The stimulus time window extends from the point at which the atrial tissue to be stimulated becomes non-refractory up to the point at which the stimulated atrial depolarization could propagate to the ventricles to cause a ventricular depolarization. The time window will vary from patient to patient, but generally will fall between the end of the atrial refractory period and the end of the ventricular refractory period. The window generally thus extends within a time period occurring between about 80 ms to about 200 ms following a normally conducted ventricular depolarization, or more or less depending on the instant heart rate. Refractory period timing and durations may vary with the individual and with the underlying heart rhythm, and thus the duration of the time window will also vary. Timing of the stimulus pulses may be based upon a preceding atrial depolarization, ventricular depolarization, or possibly both. Timing of the stimulus pulses may be predefined by the attending physician and programmed into the device.

Timing of the stimulus may also be based on a patient-specific look-up table of values dependent on physiologic variables such as heart rate, QT interval or AV interval. These patient specific values may be based on values established at baseline (rest) with empirically derived linear or non-linear extrapolations based on prior measurements, or these values could be established based on AV or QT timing measurements at various heart rates during a "learning period" in a given patient.

The location of the stimulus pulse delivery can also be important in effectively resetting the SA node or causing AV node block before the next intrinsic atrial depolarization arises from the SA node and conducts to the AV node. In other words, placement of the lead(s) and electrodes for stimulating the atrial tissue will be important. A stimulus pulse delivered at an atrial electrode site needs to depolarize the atrial myocardial tissue and propagate to the SA node to cause a resetting of the SA node before the SA node initiates the next intrinsic beat and/or reach the AV node to block a next atrial depolarization from conducting through the AV node to the ventricles. Accordingly, the timing and the location of the atrial tissue stimulus is selected to promote delivery of the stimulus during the ventricular refractory period and outside of the atrial refractory period such that the evoked atrial depolarization has adequate time to propagate to the SA node and/or AV node before the next intrinsic depolarization arises from the SA node. An electrode delivering the atrial tissue stimulus pulse may be located in close proximity, therefore, to either the SA node or the AV node.

Figure 1:
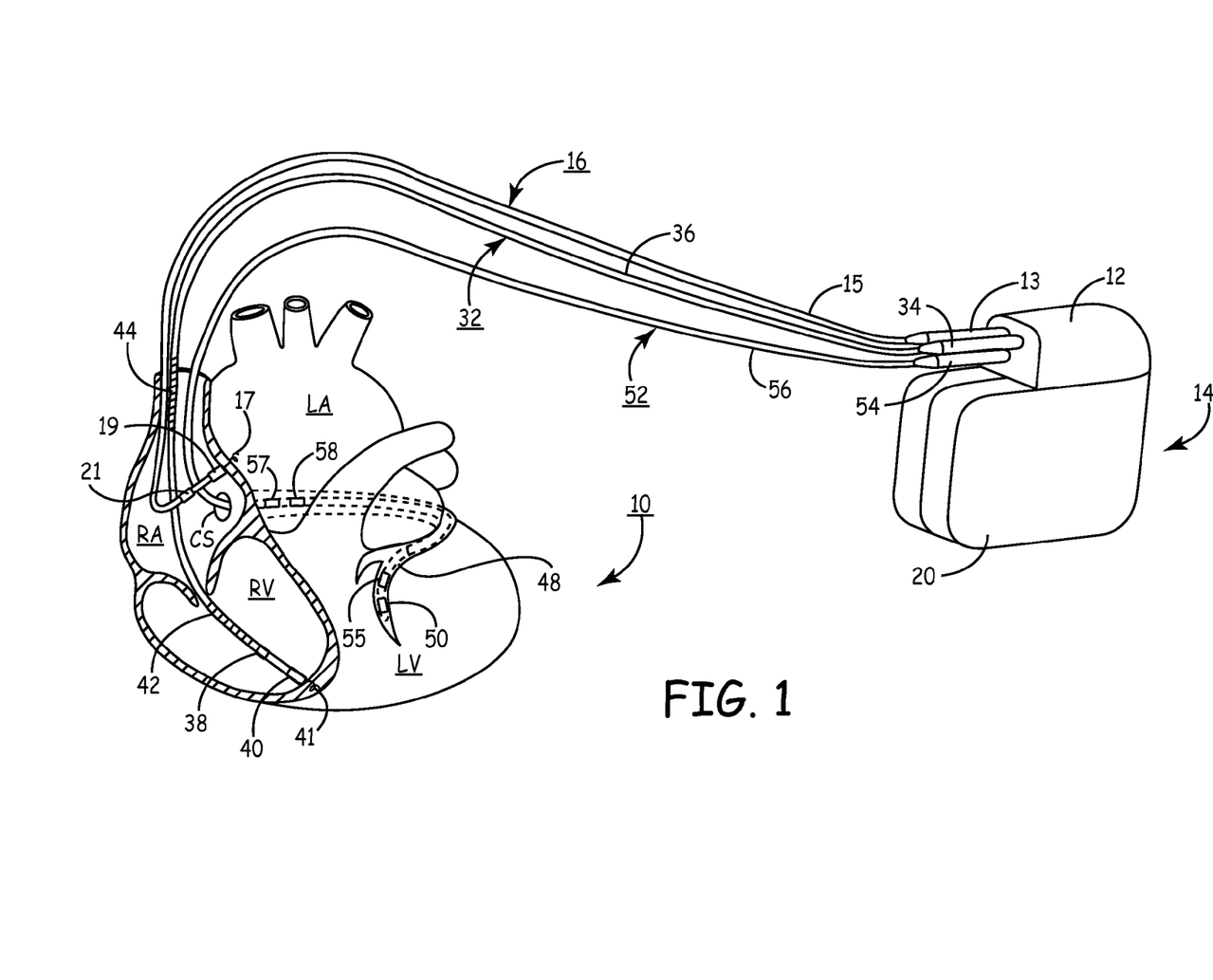
FIG. 1 depicts an implanted, multi-channel ICD according to one embodiment for use in detecting cardiac arrhythmia episodes and delivering arrhythmia therapy when appropriate.

In FIG. 1, heart 10 includes the upper heart chambers, the right atrium (RA) and left atrium (LA), and the lower heart chambers, the right ventricle (RV) and left ventricle (LV) and the coronary sinus (CS) extending from the opening in the right atrium laterally around the atria to form the great vein that extends further inferiorly into branches of the great vein. The cardiac cycle commences normally with the generation of the depolarization impulse at the SA node in the right atrial wall. The impulse then conducts through the right atrium, to the left atrial septum and reaches the AV node and the atrial septum within about 40 ms and the furthest walls of the RA and LA within about 70 ms. Approximately 50 ms following electrical activation, the atria contract, the aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent the RA or LA is also referred to as a sensed P-wave.

The depolarization impulse that reaches the AV node conducts down the bundle of His in the intra-ventricular septum after a delay of about 120 ms. The depolarization wave reaches the apical region of the heart about 20 ms later and then travels superiorly though the Purkinje fiber network over the remaining 40 ms. The aggregate RV and LV depolarization wave and the subsequent T-wave accompanying re-polarization of the depolarized myocardium are referred to as the QRST portion of the PQRST cardiac cycle complex when sensed across external ECG electrodes and displayed. When the amplitude of the QRS ventricular depolarization wave passing between a bipolar or unipolar pace/sense electrode pair located on or adjacent to the RV or LV exceeds a defined threshold amplitude, it is detected as a sensed R-wave.

FIG. 1. depicts an implanted, multi-channel ICD according to one embodiment for use in detecting cardiac arrhythmia episodes and delivering arrhythmia therapy when appropriate. The ICD 14 is implanted subcutaneously in a patient's body between the skin and the ribs. Three transvenous leads 16, 32 and 52 connect the ICD 14 with the RA, the RV and the LA and LV, respectively. Each lead has at least one electrical conductor and pace/sense electrode, and a remote indifferent can electrode 20 is formed as part of the outer surface of the housing of the ICD 14. As described further below, the pace/sense electrodes and the remote indifferent can electrode 20 (IND_CAN electrode) can be selectively employed to provide a number of unipolar and bipolar pace/sense electrode combinations for pacing and sensing functions. The depicted positions in or about the right and left heart chambers are merely illustrative. Moreover other leads and pace/sense electrodes may be used instead of the depicted leads and pace/sense electrodes that are adapted to be placed at electrode sites on or in or operative relation to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. In the context of the illustrated embodiment, the distal end of the lead 16 is located near the AV node or in the right atrial appendage, although other locations may be substituted in some cases. The bipolar endocardial RA lead 16 is formed with an in-line connector 13 fitting into a bore of ICD connector block 12 that is coupled to electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bore of ICD connector block 12 that is coupled to electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20, or one of the distal tip RV pace/sense electrode 40 and proximal ring RV pace/sense electrode 38 can be employed with the IND_CAN electrode 20 for unipolar pacing and/or sensing.

RV lead 32 further includes an RV coil electrode 42 and a superior vena cava (SVC) coil electrode 44 which are coupled to respective insulated conductors extending within lead body 36 to connector 34 engaged in a bore of ICD connector block 12. The coil electrodes 42 and 44 are electrically coupled to high voltage circuitry within ICD 14 for delivering high voltage cardioversion/defibrillation (CV/DF) shocks to heart 10. One of coil electrodes 42 or 44 may be selected in a unipolar combination with an active CAN electrode 20 for delivering a shock pulse. Alternative electrode combinations may be selected for delivering a high voltage shock pulse using one or both of coil electrodes 42 and 44. In alternative embodiments, RA lead 16 may carry a coil electrode used in delivering a high voltage shock pulse.

In this illustrated embodiment, a transvenous LV CS lead 52 is passed through a vein and the RA chamber of the heart 10, into the ostium of the CS and then inferiorly in a branching vessel of the great vein 48 to extend a pair of distal LV CS pace/sense electrodes 50 and 55 alongside the LV chamber. The LV CS lead may employ a deployable fixation mechanism or may instead rely on the close confinement within these vessels to maintain the pace/sense electrode or electrodes at a desired site. The LV CS lead 52 is coupled at the proximal end connector 54 fitting into a bore of ICD connector block 12.

The distal, LV CS pace/sense electrodes 50 and 55 may be paired in a bipolar combination or used in other electrode combinations, e.g., with the proximal ring RV indifferent pace/sense electrode 38 for delivering LV pace pulses across the bulk of the left ventricle and the intra-ventricular septum. The distal LV CS pace/sense electrodes 50 or 55 may also be paired with the distal tip RV pace/sense electrode 40 for sensing across the RV and LV.

In one embodiment, LV CS lead 52 could bear proximal LA CS pace/sense electrodes 57 and 58 positioned along the lead body 56 for positioning along the LA. The LV CS lead body may be smaller between the proximal LA CS electrodes 57 and 58 and the distal LV CS pace/sense electrodes 50 and 55. Pacing and sensing in the atria may occur using any unipolar or bipolar pair employing at least one of LA CS pace/sense electrodes 57 and 58 and/or one RA pace/sense electrodes 19 and 21.

Typically, in ICD systems of the type illustrated in FIG. 1, the electrodes designated above as "pace/sense" electrodes are used for both pacing and sensing functions. These "pace/sense" electrodes can be selected to be used exclusively as pace or sense electrodes or to be used in common as pace/sense electrodes in programmed combinations for sensing cardiac signals and delivering pace pulses along selected pacing and sensing vectors. Separate or shared indifferent pace and sense electrodes can also be designated in pacing and sensing functions. For convenience, the following description separately designates pace and sense electrode pairs where a distinction is appropriate.

Figure 2:
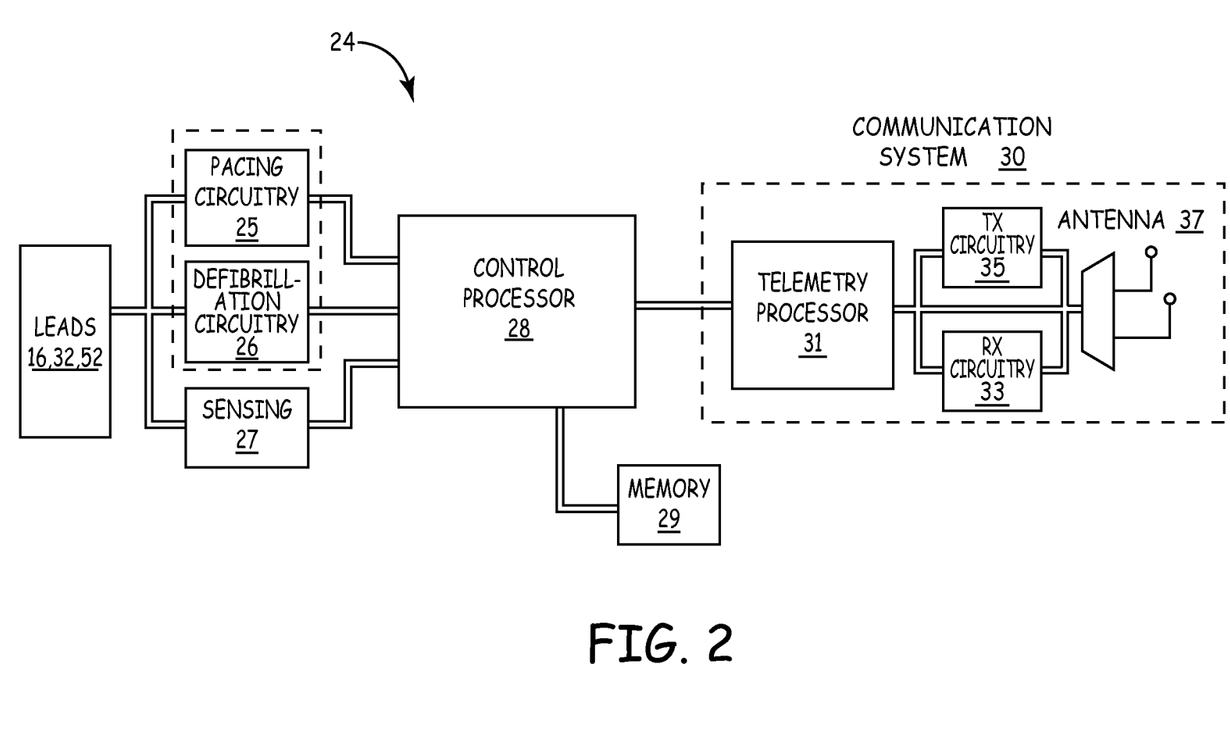
FIG. 2 is a functional block diagram of the ICD 14 shown in FIG. 1, according to one embodiment.

FIG. 2 is a functional block diagram of the ICD 14 shown in FIG. 1, according to one embodiment. Circuitry 24, located within ICD 14 of FIG. 1, includes pacing circuitry 25, defibrillation circuitry 26, sensing circuitry 27, control processor 28, memory 29, and communication system 30. Leads 16, 32 and 52 are connected to pacing circuitry 25, defibrillation circuitry 26 and sensing circuitry 27. Each lead (and in turn individual electrodes associated with each lead) coupled to the ICD may be used in multiple capacities to sense cardiac depolarizations (e.g. P-waves and R-waves), deliver pacing pulses, and deliver CV/DF shocks.

Control processor 28 receives input through sensing circuitry 27 from leads 16, 32 and 52 concerning depolarizations sensed by the electrodes connected to leads 16, 32 and 52. Based on input received from sensing circuitry 27, control processor 28 performs an arrhythmia detection algorithm for detecting arrhythmias and selecting a therapy as needed. Therapy may include providing ATP therapy using pacing circuitry 25 and selected pacing electrodes, providing defibrillation or cardioversion shocks using defibrillation circuitry 26 and a selected high voltage coil electrode, or providing no treatment at all.

Control processor 28 stores selected data to memory 29, and retrieves stored data from memory 29 as necessary in performing detection and therapy delivery algorithms and storing data relating to detected arrhythmia episodes. Communication system 30 includes telemetry processor 31, transmission circuitry 35, receiving circuitry 33, and antenna 37. Communication system 30 allows communication between ICD 14 and devices external to the patient for programming ICD 14 and retrieving data stored by ICD 14.

ICD 14 is configured to deliver pacing pulses to the atrial electrodes associated with lead 16 and/or 52 at defined time intervals during the defined time window discussed above. For purposes of the arrhythmia discrimination methods described herein, an atrial stimulus interval refers to an interval during which an atrial stimulus pulse is delivered for monitoring a response of the ventricular depolarizations for use in discriminating a cardiac arrhythmia and does not refer to intervals that may be used in delivering therapeutic pacing pulses such as bradycardia pacing pulses. The atrial stimulus interval may be initiated upon sensing an intrinsic ventricular depolarization, an intrinsic (non-paced) atrial depolarization, or some combination of both.

In some embodiments, delivery of the atrial stimulus may be triggered at a defined interval following the ventricular depolarization. It is desirable, however, that the preceding occurrence of an atrial depolarization, paced or sensed, is verified as a precondition of delivery of the stimulation pulse provided to facilitate arrhythmia discrimination. In more complex embodiments, the timing of both the atrial and ventricular depolarizations may be employed to determine the stimulus delivery time or the permitted range of delivery times (i.e., the stimulation time window).

The defined intervals chosen for delivery of the stimulus pulses may be pre-programmed by the attending physician based upon an electrophysiological study of the patient, during which myocardial refractory periods may be measured or estimated. Alternatively, the pacemaker itself may determine the optimal stimulus delivery times by varying the stimulus times within the time window and adjusting the defined stimulation intervals to produce the desired result. The desired result may be, for example, a lowering of the ventricular rate.

Activation of atrial stimulation for tachycardia discrimination may be triggered by the ICD in response to detecting a fast ventricular rate. The fast ventricular rate may be defined only by a lower rate limit. Alternatively, the fast ventricular rate that activates atrial stimulation may be additionally bounded by an upper rate limit corresponding to a VF lower rate. In other words the fast ventricular rate that activates atrial stimulation may fall into a range that is equal to or faster than a rate associated with a tachycardia detection interval but slower than a VF rate. The fast ventricular rate detected for initiating atrial stimulation may further be associated with 1:1 correspondence between atrial and ventricular sensed events, making it difficult to discriminate the fast ventricular rate as being associated with a VT or SVT.

The atrial stimulation pulses may be deactivated in response to a slowing of the ventricular rate or if the detected ventricular rate accelerates or becomes hemodynamically unstable. The determination of whether the ventricular rate has responded to the atrial stimulation pulse(s) may be made by comparing the ventricular cycle lengths (ventricular cycle lengths) prior to atrial stimulation to a ventricular cycle length occurring when an atrial stimulus pulse is delivered.

Figure 3:
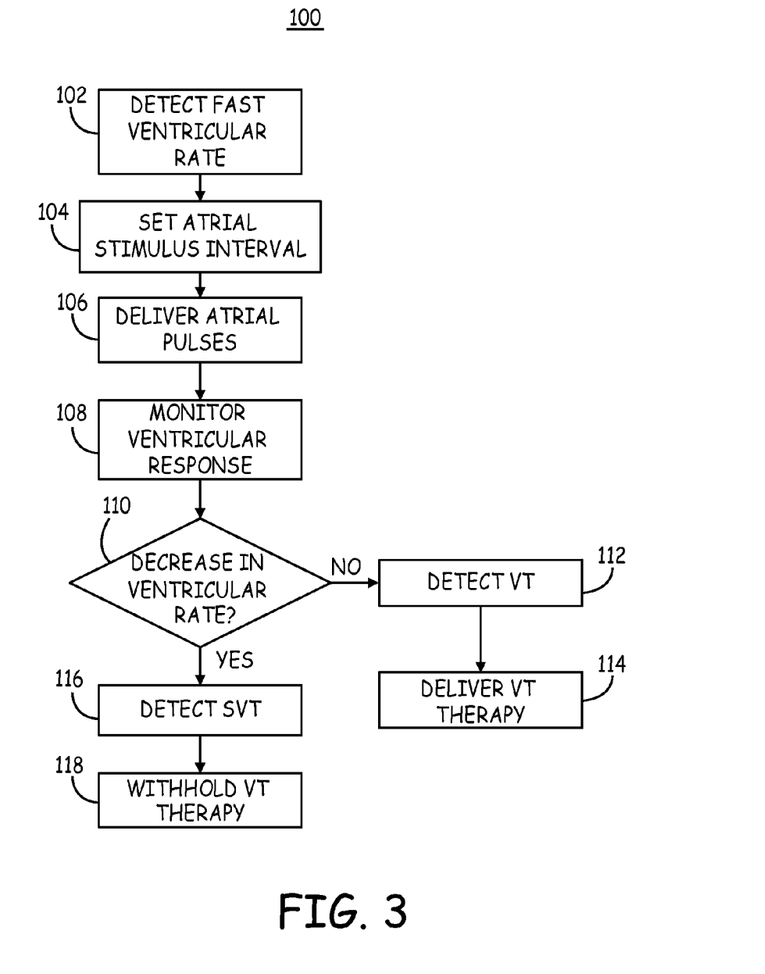
FIG. 3 is a functional flowchart 100 illustrating the operation of an ICD practicing one embodiment for arrhythmia discrimination.

FIG. 3 is a functional flowchart 100 illustrating the operation of an ICD practicing one embodiment for arrhythmia discrimination. Flow chart 100 is intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software to accomplish the described functionality in the context of any modern ICD, given the disclosure herein, is within the abilities of one of skill in the art.

Methods described in conjunction with flow chart presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

In one embodiment, the operation of the ICD to provide atrial stimulation for arrhythmia discrimination is controlled by the microprocessor responsive to software stored in memory, comprising instructions for causing the ICD to perform the described functions. The ICD detects a fast ventricular rate at block 102. The fast ventricular rate may be detected according to any preferred arrhythmia detection algorithm implemented in the ICD and is not limited to any particular rate detection method or criteria. Typically, a required number of ventricular cycle lengths (RR intervals) must be less than a tachycardia detection interval, e.g. 9 out of 12 of the most recent vetricular cycle lengths must be less than a VT detection interval, in order to detect a fast ventricular rate.

A fast ventricular rate that is suspected of possibly arising from an SVT may correspond to a venticular cycle length range defined by a maximum possible venticular cycle length interval and a minimum ventricular cycle length associated with SVT. Ventricular cycle lengths shorter than the minimum ventricular cycle length may be automatically detected as VT or VF and followed appropriately by delivery of ventricular anti-tachycardia pacing (ATP) or cardioversion/defibrillation (CV/DF) shock.

Additional criteria may be required to be satisfied at block 102 in order to detect a fast ventricular rate that triggers atrial stimulation for tachycardia discrimination. For example, other criteria may relate to factors that make the fast ventricular rate difficult to distinguish from an SVT. A fast ventricular rate may be suspected of being SVT when indiscriminate R-wave morphology or 1:1 P-wave to R-wave correspondence is identified. As such, other requirements that may be applied at block 102 in detecting a fast ventricular rate that activates atrial stimulation for arrhythmia discrimination may include morphology or event pattern-based criteria. If ventricular R-wave morphology analysis does not confirm a morphology corresponding to VT or VF, the fast ventricular rate may be a suspected SVT causing activation of atrial stimulation. In still other embodiments, if the ratio of sensed atrial P-waves to sensed ventricular R-waves are in 1:1 correspondence, and a fast ventricular rate is detected, atrial stimulation for tachycardia stimulation is activated.

Upon detecting the fast ventricular rate (along with any other requirements for activating atrial stimulation), an atrial stimulus interval is set at block 104 to deliver atrial stimulus pulses during the window of time in which the ventricles are still in refractory and the atria are not, on one or more cardiac beats. The atrial stimulus interval may be in timed relation to a ventricular sense event and/or an atrial sense event as described above. The atrial stimulus interval may be timed based on measured refractory periods in an individual patient or based on clinical data from a population of patients.

At block 106 atrial stimulation pulses are delivered, carefully timed to occur during ventricular refractory period for resetting the SA node or blocking AV node conduction. The atrial stimulation pulses may include a single pulse per cardiac cycle or a train of pulses per cardiac cycle and may be delivered for a single cardiac cycle or a predetermined number of cardiac cycles, e.g. on the order of approximate 3 to 10 cardiac cycles, to allow the ventricular response to the atrial stimulus pulse(s) to be measured at block 108.

A single pulse, when properly timed and delivered at an appropriate location, can be effective in causing a slowing of the ventricular rate during an SVT. However, a train of pulses may be delivered at block 106 during a window of time expected to be within the ventricular refractory period and outside the atrial refractory period. An exact timing of a single atrial stimulus pulse for achieving SA node reset or AV node block may vary with heart rate, electrode location, between patients, and with other factors. By delivering a train of pulses during the above-mentioned window of time, the window of time is effectively "scanned" by all of the pulses such that at least one of the pulses may effectively reset the SA node or block the AV node. Furthermore, an atrial stimulus pulse or a train of pulses may be delivered at more than one location in the atria at the same time or at slightly different times.

Generally, if the fast ventricular rate is due to an SVT, a ventricular response to the atrial stimulus pulses will be detected. A ventricular response will be a slowing of the ventricular rate which can be measured as an increase in ventricular cycle lengths or detecting a change in the ratio of atrial to ventricular sensed depolarizations. If the fast ventricular rate is arising from the ventricles, i.e. a true VT, no ventricular response to the atrial stimulus pulses will be detected at block 108. In some cases, the ventricular rate may accelerate during atrial stimulation if the VT worsens. In other cases, the ventricular rate will remain relatively unchanged during atrial stimulation.

In one embodiment, the ventricular cycle length is measured during each cardiac cycle associated with an atrial stimulus pulse at block 108. An average, maximum, minimum or range of ventricular cycle lengths associated with an atrial stimulus pulse may be measured and compared, at block 110, to an average, minimum or range of ventricular cycle lengths measured prior to delivering atrial stimulus pulses and contributing to the detection of the fast ventricular rate. Alternatively, the ventricular cycle lengths occurring during atrial stimulation may be compared to predefined ventricular tachycardia detection intervals at block 110 to determine if the ventricular cycle lengths become longer than a tachycardia detection interval.

If the ventricular cycle lengths during atrial stimulation are found to increase compared to prior ventricular cycle lengths or a tachycardia detection interval at decision block 110, the fast ventricular rate is detected as SVT at block 116. VT therapy is withheld at block 118. If the ventricular cycle lengths during atrial stimulation do not increase, i.e. if a decrease in the rate of sensed ventricular depolarizations is not detected at block 110, VT is detected at block 112. VT therapy is delivered at block 114 according to a programmed therapy delivery menu.

In an alternative embodiment, the ratio of sensed ventricular depolarizations to atrial depolarizations (sensed and paced) is determined at block 108 for detecting a decrease in the ventricular rate at block 110. If the atrial stimulus pulse causes a resetting of the SA node or AV node block, a 1:2 ratio, or other changed ratio, of ventricular to atrial depolarizations will occur. The atrial depolarization associated with the atrial stimulus pulse will not be conducted to the ventricles whereas the next intrinsic atrial depolarization arising from the SA node will conduct to the ventricles. In some cases, the ratio of ventricular to atrial depolarization may change from 1:1 during a conducted fast ventricular rate to, for example, 1:3 or even 2:3, during atrial stimulus delivery depending on the duration and stability of the refractory periods.

If at least two atrial depolarizations, one associated with an intrinsic atrial depolarization and one associated with the atrial stimulus pulse, occur during a single ventricular cycle length, a ventricular slowing has occurred in response to the atrial stimulus. Accordingly, monitoring the ventricular response at block 108 may include monitoring a ratio of atrial and ventricular depolarization events. Detecting a decrease in the ventricular rate at block 110 in response to an atrial stimulus pulse includes detecting more than one atrial depolarization during a ventricular cycle length associated with an atrial stimulus pulse delivered therein.

In some embodiments, an examination of R-wave morphology, a change in P-R intervals, or change in a conduction sequence as determined from EGM signals sensed at different myocardial sites may be useful in distinguishing R-waves that are conducted from an atrial stimulus pulse or conducted from an intrinsic atrial event. As such, the response monitored at block 108 may include measurements of P-R intervals and/or EGM morphology analysis at one or more ventricular sensing sites.

In some cases, delivery of one or more atrial stimulus pulses may effectively terminate an SVT. Termination of a SVT in response to the atrial stimulus will also result in a slowing of the ventricular rate (which can be detected at block 110) when the fast ventricular rate was being conducted from the atria. As such, the detection of SVT is made at block 116 and VT therapy is withheld at block 118 when atrial stimulus pulses cause a termination of the SVT.

Figure 4:
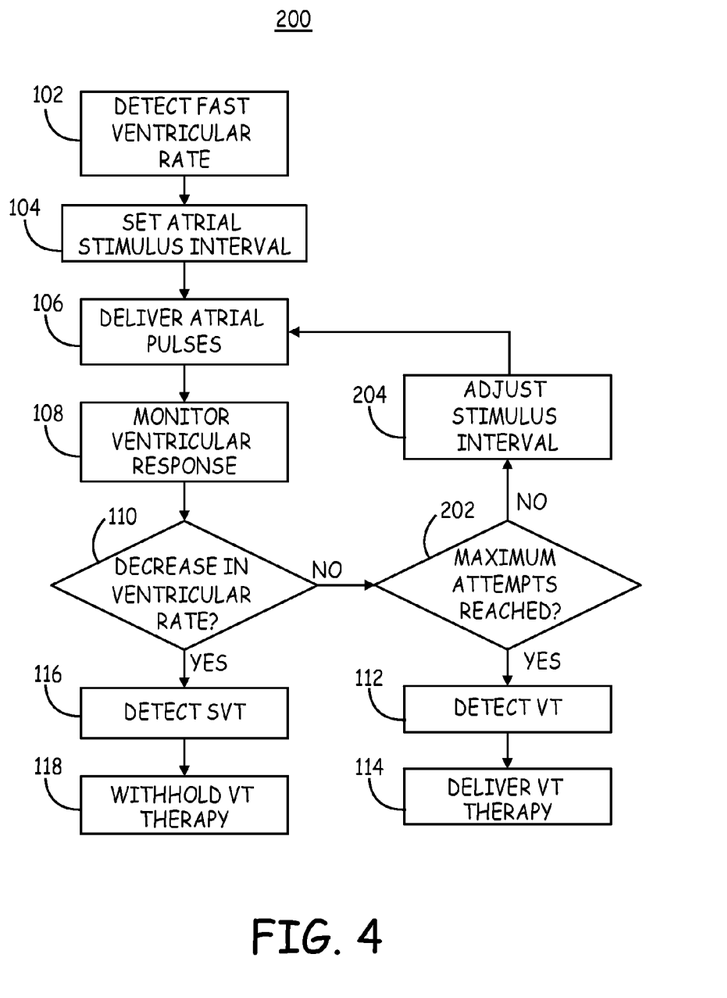
FIG. 4 is a flow chart 200 of an alternative embodiment of a method for discriminating cardiac events.

FIG. 4 is a flow chart 200 of an alternative embodiment of a method for discriminating cardiac events. In FIG. 4, blocks 102 through 118 correspond to identically numbered blocks shown in FIG. 3. In most embodiments, it is anticipated that the parameters of the individual atrial stimulation pulses (width, amplitude, etc.) will be determined at implant and programmed into the ICD memory by the attending physician. However, in some embodiments mechanisms for optimizing these parameters may be employed. In particular, an atrial stimulus interval may be adjusted during a tachycardia episode if no ventricular response is detected during delivery of one or more atrial stimulus pulses.

If no decrease in ventricular rate is detected in response to atrial stimulus pulses delivered at an initial atrial stimulus interval (and other pulse parameters), and the fast ventricular rate is tolerated by the patient, i.e. hemodynamically stable, adjustments to the atrial stimulus may be made to further verify that the fast ventricular rate is not being conducted from atrial tissue. Adjustments to the atrial stimulus may include changing a pulse delivery electrode, changing a pulse amplitude, width or pulse number.

For example, the atrial stimulus interval may be adjusted at block 204 when no ventricular response to atrial stimulation is detected. At block 202, if a maximum number or time duration of delivering atrial stimulus pulses has not been reached, the atrial stimulus interval (or another atrial stimulus parameter) is adjusted at block 204.

The atrial stimulus interval may be adjusted one or more times within the range of the above-discussed stimulus time window to promote delivery of the stimulus pulse(s) during ventricular refractory and outside atrial refractory for effective resetting of the SA node and/or AV node block.

Instead of using a fixed atrial stimulus interval during the delivery of atrial pulses at block 106, the atrial stimulus interval may be increased (or decreased) in predetermined increments, e.g. 10 ms, on successive cardiac beats. At block 108, the ventricular response is monitored to determine if, on any one or more beats during atrial stimulus delivery, a slowing of the ventricular rate is detected. If the fast ventricular rate is a true VT, it is desirable to make that determination in as short as time as possible. As such, it may be desirable to use a variable atrial stimulus interval on a series of successive beats to effectively "scan" the expected window of time that is outside atrial refractory but within ventricular refractory and determine if any ventricular response to a properly timed atrial stimulus within the window can be achieved.

The atrial stimulus interval may be increased or decreased on each successive beat, every other beat, every third beat, etc. to allow the ventricular response to successive adjustments of the atrial stimulus interval to be monitored. If a ventricular response is detected during the successive adjustments, the atrial stimulus may be terminated before all increments or decrements are applied, and an SVT detected.

If a maximum number of attempted atrial stimulus intervals, maximum number of atrial pace pulses, maximum duration of atrial pulse delivery or other maximum limit for delivering atrial pulses during a detected tachycardia is reached at block 202, without identifying a ventricular response to the atrial pulse delivery, VT is detected at block 112. A VT therapy is delivered at block 114.

Thus, a medical device and associated method for discriminating tachycardia have been presented in the foregoing description with reference to specific embodiments. It is appreciated that various modifications to the referenced embodiments may be made without departing from the scope of the disclosure as set forth in the following claims.

The invention claimed is:

1. A method for discriminating cardiac events in an implantable medical device, comprising:
    sensing atrial and ventricular depolarizations having associated refractory periods thereafter;
    detecting a fast ventricular rate in response to the sensed ventricular depolarizations;
    delivering a stimulus pulse to atrial tissue in response to detecting the fast ventricular rate, the stimulus pulse being delivered within the associated refractory period of the ventricle but outside of the associated refractory period of the stimulated atrial tissue;
    determining a ventricular response to the atrial tissue stimulus pulse; and
    discriminating a cardiac event associated with the detected fast ventricular rate in response to the ventricular response to the delivered stimulus pulse.

2. The method of claim 1, comprising defining a time interval following the sensed ventricular depolarizations, wherein the stimulus pulse is delivered during the defined window.

3. The method of claim 1, comprising defining a time interval following an atrial depolarization, wherein the stimulus pulse is delivered upon expiration of the time interval.

4. The method of claim 1, wherein detecting the ventricular response comprises detecting a change in a rate of the sensed ventricular depolarizations.

5. The method of claim 1, wherein detecting the ventricular response comprises:
sensing a next ventricular depolarization subsequent to delivering the atrial tissue stimulus pulse, the next ventricular depolarization having an associated ventricular cycle length extending from a preceding ventricular depolarization to the next ventricular depolarization; and
discriminating the cardiac event in response to the associated ventricular cycle length.

6. The method of claim 1, further comprising:
determining a first ventricular tachycardia cycle length prior to the delivered stimulus pulse;
determining a second ventricular cycle length, the second ventricular cycle length being between consecutive ventricular depolarizations during delivery of the stimulus pulse; and
comparing the first ventricular tachycardia cycle length to the second ventricular cycle length, wherein discriminating the cardiac event comprises:
discriminating the event as a supraventricular event if the second ventricular cycle length is one of greater than or less than the first ventricular tachycardia cycle length; and
discriminating the event as a ventricular tachycardia event in response to the second ventricular cycle length being equal to the first ventricular tachycardia cycle length.

7. The method of claim 1, further comprising:
determining a number of atrial depolarizations occurring during a ventricular cycle length extending between two consecutively sensed ventricular depolarizations and having the atrial tissue stimulus pulse delivered during the ventricular cycle length; and
discriminating the cardiac event as a supraventricular event in response to more than one atrial depolarization occurring during the ventricular cycle length.

8. The method of claim 1, further comprising withholding a ventricular therapy if the cardiac event is discriminated as a supraventricular cardiac event.

9. The method of claim 1, wherein delivering a stimulus pulse comprises delivering a train of stimulus pulses.

10. The method of claim 1, wherein delivering the stimulus pulse comprises:
delivering the pulse at a stimulus pulse interval;
adjusting the stimulus pulse interval; and
delivering a next stimulus pulse on a next cardiac beat within the associated refractory period of the ventricle but outside of the associated refractory period of the stimulated atrial tissue at the adjusted stimulus pulse interval.

11. The method of claim 1, further comprising:
establishing a look-up table of timing intervals following a sensed depolarization for delivering the atrial stimulus pulse, each of the timing intervals associated with a duration of a cardiac interval;
determining a cardiac interval in response to detecting the fast ventricular rate;
determining, from the look-up table, a timing interval associated with the measured cardiac interval; and
delivering the atrial stimulus pulse upon expiration of the determined timing interval.

12. The method of claim 11, wherein the cardiac interval corresponds to one of a heart rate, a QT interval and an AV interval.

13. A medical device for discriminating a cardiac event, comprising:
sensing circuitry for sensing atrial and ventricular depolarizations having associated refractory periods thereafter;
pacing circuitry for delivering stimulus pulses to atrial tissue; and
a processor configured to:
detect a fast ventricular rate in response to the sensed ventricular depolarizations,
in response to detecting the fast ventricular rate, set an atrial pacing time interval that expires in an excitation window that extends from an end of the atrial refractory period to an end of the ventricular refractory period,
upon expiration of the atrial pacing interval deliver a stimulus pulse to atrial tissue within the associated refractory period of the ventricle but outside of the associated refractory period of the stimulated atrial tissue, determine a ventricular response to the atrial tissue stimulus pulse; and
discriminate a cardiac event associated with the fast ventricular rate based on the ventricular response to the atrial tissue stimulus pulse.

14. The apparatus of claim 13, wherein the processor establishes a time interval following the sensed ventricular depolarizations and wherein the stimulus pulse is delivered during the defined window.

15. The apparatus of claim 13, wherein the processor establishes the atrial pacing time interval following an atrial depolarization and wherein the stimulus pulse is delivered upon expiration of the time interval.

16. The apparatus of claim 13, wherein detecting the ventricular response comprises detecting a change in a rate of the sensed ventricular depolarizations.

17. The apparatus of claim 13, wherein the process is further configured to sense a next ventricular depolarization subsequent to delivering the atrial tissue stimulus pulse, the next ventricular depolarization having an associated ventricular cycle length extending from a preceding ventricular depolarization to the next ventricular depolarization, and discriminate the cardiac event in response to the associated ventricular cycle length.

18. The apparatus of claim 13, wherein the processor is further configured to determine a first ventricular tachycardia cycle length prior to the delivered stimulus pulse, determine a second ventricular cycle length, the second ventricular cycle length being between consecutive ventricular depolarizations during delivery of the stimulus pulse, and compare the first ventricular tachycardia cycle length to the second ventricular cycle length, wherein discriminating the cardiac event comprises:
discriminating the event as a supraventricular event if the second ventricular cycle length is one of greater than or less than the first ventricular tachycardia cycle length; and
discriminating the event as a ventricular tachycardia event in response to the second ventricular cycle length being equal to the first ventricular tachycardia cycle length 19. The apparatus of claim 13, wherein the processor is further configured to determine a number of atrial depolarizations occurring during a ventricular cycle length extending between two consecutively sensed ventricular depolarizations and having the atrial tissue stimulus pulse delivered therebetween, and discriminate the cardiac event as a supraventricular event if more than one atrial depolarization occurs during the ventricular cycle length.

20. The apparatus of claim 13, wherein delivering a stimulus pulse comprises delivering a train of stimulus pulses.

21. The apparatus of claim 13, wherein the processor is further configured to deliver the pulse at a stimulus pulse interval, adjust the stimulus pulse interval, and deliver a next stimulus pulse on a next cardiac beat within the associated refractory period of the ventricle but outside of the associated refractory period of the stimulated atrial tissue at the adjusted stimulus pulse interval.

22. The apparatus of claim 13, wherein the processor is further configured to establish a look-up table of timing intervals following a sensed depolarization for delivering the atrial stimulus pulse, each of the timing intervals associated with a duration of a cardiac interval, determine a cardiac interval in response to detecting the fast ventricular rate, determine, from the look-up table, a timing interval associated with the measured cardiac interval, and deliver the atrial stimulus pulse upon expiration of the determined timing interval.

23. The apparatus of claim 22, wherein the cardiac interval corresponds to one of a heart rate, a QT interval and an AV interval.

24. A non-transitory computer-readable medium storing a set of instructions for performing a method, the method comprising:
- sensing atrial and ventricular depolarizations having associated refractory periods thereafter;
- detecting a fast ventricular rate in response to the sensed ventricular depolarizations;
- delivering a stimulus pulse to atrial tissue in response to detecting the fast ventricular rate, the stimulus pulse being delivered within the associated refractory period of the ventricle but outside of the associated refractory period of the stimulated atrial tissue;
- determining a ventricular response to the atrial tissue stimulus pulse; and
- discriminating a cardiac event associated with the detected fast ventricular rate in response to the ventricular response to the delivered stimulus pulse.

* * * * *